United States Patent [19]

Engel

[11] Patent Number: 4,848,353
[45] Date of Patent: Jul. 18, 1989

[54] ELECTRICALLY-CONDUCTIVE, PRESSURE-SENSITIVE ADHESIVE AND BIOMEDICAL ELECTRODES

[75] Inventor: Michael R. Engel, Maplewood, Minn.

[73] Assignee: Minnesota Mining and Manufacturing Company, St. Paul, Minn.

[21] Appl. No.: 902,396

[22] Filed: Sep. 5, 1986

[51] Int. Cl.⁴ .......................... A61B 5/04; A61N 1/04
[52] U.S. Cl. .............................. 128/640; 128/303.13; 128/798; 252/500; 427/2
[58] Field of Search ................. 128/639–641, 128/798, 802, 803, 303.13; 427/2; 252/500

[56] References Cited

U.S. PATENT DOCUMENTS

| | | | |
|---|---|---|---|
| 4,274,420 | 6/1981 | Hymes | 128/641 |
| 4,352,359 | 10/1982 | Larimore | 128/640 |
| 4,391,278 | 7/1983 | Cahalan et al. | 128/640 |
| 4,451,630 | 5/1984 | Atkinson et al. | 526/261 |
| 4,524,087 | 6/1985 | Engel | 427/2 |
| 4,539,996 | 9/1985 | Engel | 128/640 |
| 4,543,958 | 10/1985 | Cartmell | 128/640 |
| 4,554,924 | 11/1985 | Engel | 128/640 |
| 4,602,640 | 7/1986 | Wada et al. | 128/639 |
| 4,674,512 | 6/1987 | Rolf | 128/640 |

FOREIGN PATENT DOCUMENTS

| | | | |
|---|---|---|---|
| 1181582 | 1/1985 | Canada | 128/640 |
| 0081846 | 12/1982 | European Pat. Off. | |
| 8018272 | 5/1980 | Japan | |
| 82/6478 | 7/1983 | South Africa | |
| 2115431 | 9/1983 | United Kingdom | |
| 2130743 | 6/1984 | United Kingdom | |

Primary Examiner—Lee S. Cohen
Attorney, Agent, or Firm—Donald M. Sell; Walter N. Kirn; Dale E. Hulse

[57] ABSTRACT

An electrically-conductive, pressure-sensitive adhesive composition having a polymeric matrix comprised of copolymers of hydrogen bond donating monomer (for example acrylic acid) and hydrogen bond accepting monomers (for example N-vinylpyrrolidone) is disclosed. The polymeric matrix is homogeneously mixed with a electrically-conductive plasticizing solution comprised of from 0% to 98% by weight water-soluble, polar organic compound (for example glycerol), 2% to 100% by weight water, and 0 to 12% by weight water-soluble salt. The compsition contains from about 12% to 50% by weight non-volatile copolymer matrix and the hydrogen bond donating sites on the copolymer matrix are from about 5% to about 95% neutralized. Free radical polymerization methods of making the composition and biomedical electrodes incorporating the composition are also described.

18 Claims, 2 Drawing Sheets

ELECTRICALLY-CONDUCTIVE, PRESSURE-SENSITIVE ADHESIVE AND BIOMEDICAL ELECTRODES

FIELD OF THE INVENTION

This invention relates to electrically-conductive, pressure-sensitive adhesive compositions having a polymeric matrix comprised of copolymers of hydrogen bond donating monomers and hydrogen bond accepting monomers. In another aspect, the invention relates to a biomedical electrode having a pressure-sensitive adhesive as the electrically-conductive, skin interfacing material.

BACKGROUND OF THE INVENTION

An adhesive composition which serves to adhere a biomedical electrode to skin and to establish an electrical connection between skin and an electrical medical apparatus desirably has multiple characteristics which are difficult to achieve in one composition. The composition should have the characteristics of a good medical adhesive and those of a good electrical conductor.

A good medical pressure-sensitive adhesive needs to be dermally non-irritating, sufficiently plastic and tacky to wet skin and adhere, and sufficiently cohesive both to resist shear and peel forces and to pull away from skin without leaving a residue. Compositions which make good medical adhesives are well known. Exemplary classes are polyvinyl ethers and copolymers of acrylic acid and isooctylacrylate. Copolymers used on many commercially available medical tapes include adhesives made from isooctylacrylate and up to ten percent by weight acrylic acid or N-vinylpyrrolidone. An exemplary formulation is a copolymer of 96% isooctylacrylate and 4% acrylic acid; another adhesive is based on 91% isooctylacrylate and 9% N-vinylpyrrolidone. While these formulations make excellent medical adhesives, they are not suitable for electrically-conductive adhesives. Conductive adhesives require a substantial amount of plasticizing electrically-conductive liquid. The plasticizing electrically-conductive liquid is polar and usually has ionic species in solution. The isooctylacrylate and acrylic acid or N-vinylpyrrolidone copolymers are not crosslinked and are not soluble in water and other polar liquids. If they are mixed with polar liquids and ionic solutions, phase separation results.

The electrical properties desired of a conductive, pressure-sensitive adhesive relate to its ability to transmit ionic electric current to or from the body and, in co-operation with a conductor, to convert ionic current to electric current or electric current to ionic current. The ability of the compositon to accurately transmit the ionic electric current generated by biomedical events is very important. To optimize electrical performance, a low impedance at the interface of the composition and the skin is desirable. Also important is the ability of the biomedical electrode to translate ionic current to electrical current and electrical current to ionic current. In many instances this translation is effected by means of an electrochemical reaction. For example, in a classic silver/silver chloride system the conductor is a layer of metallic silver having a thin layer of silver chloride on its surface, and the electrolyte medium (conductive gel or conductive adhesive) contains chloride ions. The electrical performance of this system depends in part on the concentration and mobility of ionic species in the composition. The hydrogen ion concentration is also relevant. In other systems, the translation may be effected by capacitive coupling. In that circumstance, the charge density of the electrode is important to the ability of the electrode to translate the signals encountered. Here again, the concentration of ionic species is important to good performance. For example, in a patient grounding plate large alternating currents (typically 0.1-1A at about 500 KHz) are encountered. In these conditions, capacitive coupling is possible and the presence of ionic species facilitates transfer.

Conductive pressure-sensitive adhesives are shown in many patents. U.S. Pat. No. 4,274,420 to Hymes, U.S. Pat. No. 4,352,359 to Larimore, and U.S. Pat. Nos. 4,524,087, 4,539,996, and 4,554,924 to Engel are exemplary. Two of the Engel Patents (U.S. Pat. Nos. 4,524,087 and 4,539,996) disclose an electrically-conductive adhesive formed by an essentially solventless free radical polymerization of an adhesive precursor having a polyhydric alcohol, at least on ionic monomer, a crosslinker, and an initiator. Non-ionic comonomers may be included. Ionic monomers listed are salts of $\alpha,\beta$-unsaturated carboxylic acids such as potassium and sodium acrylate and sodium methacrylate. Non-ionic comonomers listed are acrylic acid, methacrylic acid, and hydroxyethyl methacrylate.

The third Engel patent (U.S. Pat. No. 4,554,924) discloses a conductive adhesive formed by an essentially solventless free radical polymerization of an adhesive precursor having a polyhydric alcohol, at least one non-ionic monomer, an initiator, a crosslinker, and an ionizable salt present in an amount sufficient to render the composition conductive. Non-ionic monomers shown are acrylic acid, methacrylic acid, hydroxyethyl methacrylate, and N-vinylpyrrolidone. The specification states that the non-ionic polymerization material may comprise one non-ionic monomer or a mixture of non-ionic monomers. Also, it says ionic monomers may be included.

Conductive adhesives made according to the Engel patents are used in patient grounding plates, transcutaneous electrical nerve stimulation (TENS) electrodes, and diagnostic electrocardiogram (EKG/ECG) electrodes. While these adhesives provide excellent adhesive and electrical properties for some applications, optimizing the electrical properties without adversely affecting adhesion properties has not proved possible. Experience has shown that increasing the water content of the Engle adhesive compositions to about 25% improves the electrical performance of electrodes coated with the adhesives. The reason for this empirical observation is not known; one possible explanation is that increased water facilitates wetting of skin, thereby reducing skin impedance. Unfortunately, increasing water content to optimum levels for electrical performance is found to decrease the initial tack and cohesive strength of the polymer, resulting in poor skin adhesion and residue left on the skin when the electrode is removed. While tackifiers may be used, they have not been found particularly helpful in optimizing the electrical and adhesive properties.

Another conductive adhesive is disclosed in U.K. Patent Appln. 2,115,431 (published Sept. 7, 1983). That publication describes adhesives formed by dissolving or dispersing polymers in a plasticizing liquid and subjecting the mixture to radiation energies at least equivalent to 100,000 electron volts (X-ray, gamma and beta ray, and electron beam irradiation). The conductive adhesive described is prepared from polyvinylpyrrolidone, polyethylene glycol, magnesium acetate, methyl paraben, propyl paraben, FD&C Blue #2 and water.

A commercially electrically-conductive adhesive sold under the trademark Polyhesive ™ (Valleylab, Inc., Boulder, CO) is believed to be made according to the disclosure of U.K.. Appn. 2,115,431. That adhesive exhibits good electrical properties but performs poorly as a biomedical adhesive. The initial adhesion to skin is not strong enough for many applications and the adhesive tends to lose moisture with time resulting in loss of adhesion at the edges of an electrode.

The conductive adhesives described above are crosslinked swellable polymeric matrices. When a polymeric matrix has sufficient crosslinking it can be fully swelled without dissolving. When these crosslinked materials are swelled with water they are called hydrogels. A non-adhesive hydrogel used for contact lenses is disclosed in U.K. Patent Appl. 2,130,743 (published June 6, 1984) and may be made as a terpolymer of a monomer mixture comprising N-vinylpyrrolidone, a short chain alkyl acrylate or methacrylate, and a short chain unsaturated carboxylic acid. That application requires the N-vinylpyrrolidone and the ester to make up the majority of the monomer mixture. It recommends the acid monomer not exceed 10% of the monomer mixture. The examples all have acid monomers comprising less than 4% (by weight) of the total monomers and less than 5% (by weight) of the N-vinylpyrrolidone. U.S. Pat. No. 4,451,630 shows another terpolymer used for contact lenses having N-vinylpyrrolidone and a short chain unsaturated acrylic acid. The monomer mixture for that terpolymer is N-vinylpyrrolidone (25 to 50% by weight) methacrylic or acrylic acid (up to 5% by weight), a triazine crosslinker (0.1 to 1% by weight), and hydroxy alkyl acrylate or methacrylate (balance). The examples have acid monomer comprising less than 2% by weight of the total monomer mixture and less than 5% by weight of the N-vinylpyrrolidone.

A class of adhesives that can be dispersed or dissolved in polar solutions including water is the class of repulpable adhesives. They are generally not crosslinked. One such repulpable adhesive is made with a comonomer of butyl acrylate and methyl diethanol ammonium acrylate. While ionic species may be somewhat soluble in these adhesives sufficient ionic concentration and mobility for optimal electrical performance has not been possible when the total water content is low enough to avoid dispersion of the polymers.

Another repulpable adhesive is soluble in both acid and basic solutions. Japanese Appl. No. 80-18772 (published May 17, 1980) describes a non-conductive adhesive that has a copolymer made from a polymerizable vinyl carboxyl contaning monomer and a vinylpyrrolidone, vinylpyridine or other basic monomer. The copolymer contains acid functional groups and alkaline functional groups in a prescribed ratio of 60-99.5% acid monomer to 40-0.5% basic monomer. The adhesive contains a water soluble plasticizer such as a polyhydric alcohol.

Mixtures of polymers rich in hydrogen bond donating groups with polymers rich in hydrogen bond accepting sites are known to be insoluble in water. For example, polyacrylic acid, a polymer rich in hydrogen bond donating sites, and polyvinylpyrrolidone, a polymer rich in hydrogen bond accepting sites, are each soluble in water. When solutions containing the two polymers are mixed, a partially swelled matrix rapidly precipitates out of solution.

SUMMARY OF THE INVENTION

The present invention overcomes the problem of adversely affecting adhesion when optimizing electrical properties. The composition of the present invention displays adhesion properties far better than the prior art Engel and Polyhesive ™ conductive adhesives together with electrical properties equivalent to or better than those of the prior art Engel and Polyhesive ™ adhesives.

The electrically-conductive, pressure-sensitive adhesive compositions of the present invention are a homogeneous mixture of a copolymer matrix and a plasticizing, electrically-conductive solution.

The copolymer matrix is formed from a free radical polymerizable adhesive precursor having at least one water-soluble hydrogen bond donating monomer, at least one water-soluble hydrogen bond accepting monomer, and a free radical initiator of either the photo or thermal class. The ratio of hydrogen bond donating sites to hydrogen bond accepting sites in the monomer mixture is from about 1:3 to about 6:1. The weight ratio of the hydrogen bond donating monomer to the hydrogen bond accepting monomer is from about 1:2 to about 3:1.

The plasticizing, electrically-conductive solution contains from 0 to 98% by weight water-soluble polar organic compound, 2 to 100% by weight water, and 0 to 12% by weight water-soluble salt.

The adhesive composition contains from 12% to 50% by weight non-volatile copolymer matrix. The acidic hydrogen bond donating sites on the copolymer are from 0.5% to 95% neutralized. The composition is substantially homogeneous, i.e., it has essentially no phase separation, and provides a pressure-sensitive adhesive. While small areas of phase separation, observable in a web of adhesive composition as opaque patches, may be acceptable for certain applications, complete homogeneity is far preferred.

The composition does not need to be covalently crosslinked, but a crosslinker may be used. A multifunctional crosslinker may be added to the adhesive precursor up to about 0.5% by weight.

The composition may be made by preparing an adhesive precursor and polymerizing the monomers with a free radical reaction. The adhesive precursor comprises at least one water-soluble hydrogen bond donating monomer, at least one water-soluble hydrogen bond accepting monomer, a free radical initiator of either the photo or thermal class and a plasticizing, electrically-conductive solution. The plasticizing, electrically-conductive solution has from 0 to 98% by weight water-soluble polar organic compound, from 2 to 100% water, and from 0 to 12% soluble salt. The precursor is comprised of from 12% to 50% by weight monomers. Preferably the precursor is comprised of about 20% by weight monomers and the hydrogen bond accepting monomer and the hydrogen bond donating monomer are present in equal amounts. Acidic hydrogen bond donating sites are from 5 to 95% neutralized. Where covalent crosslinking is desired the adhesive precursor may further comprise up to about 0.5% by weight multifunctional crosslinking monomer.

The monomers suitable for this invention when copolymerized display sufficient interaction in the presence of water and polar plasticizers to produce improved physical properties (adhesion, cohesion) without phase separation.

The hydrogen bond donating monomers useful in the present invention include any polymerizable monomer having at least one hydrogen bond donating group such as unsaturated organic acids. Polymerizable ethylenically unsaturated organic acids such as carboxylic acids, phosphonic and phosphinic acids, and sulfonic acids may be used. The monomer should be soluble in the plasticizing electrically conducting solution. Short chain $\alpha,\beta$-ethylenically unsaturated carboxylic acids having from 3 to 8 carbon atoms are preferred. Especially preferred are acrylic acid and methacrylic acid.

The hydrogen bond accepting monomers useful in the present invention include any polymerizable monomer having at least one hydrogen bond accepting group. N-vinyl amides, N-vinyl lactams and $\alpha,\beta$-unsaturated amides such as acrylamide or substituted acrylamides may be used. The monomer should be soluble in the plasticizing electrically conducting solution. N-vinylpyrrolidone is preferred.

The nature of the interaction among the chains in the copolymer matrix are not understood. Without intending to be limited to any mechanistic theory, the interaction is believed to involve hydrogen bonding between chains in the copolymer matrix. Hydrogen bonds are formed, in general, between a donor molecule containing a hydrogen attached to an oxygen, nitrogen, or fluorine atom and an acceptor molecule containing oxygen, nitrogen, or fluorine atom. These bonds are weaker than covalent bonds and tend to rapidly break and form in solution.

The strength of a particular hydrogen bond is related in general to the acidity of the hydrogen on the donor group, and the basicity of the acceptor group plus any steric considerations effecting the geometry of the bond.

The net effect of such hydrogen bonding on physical properties of polymeric donors and acceptors is difficult to quantitatively predict due to the complex steric consideration in systems. Where the hydrogen bond accepting and donating materials are dissolved in highly polar solvents which also readily form hydrogen bonds (water, glycerol) the effect of hydrogen bonding among the various components is particularly difficult to predict. In such systems, an equilibrium exists between all the possible interactions.

The plasticizing electircally-conductive solution is "electrically-conductive" if it contains polar or ionic species effective to provide sufficient electrical conductivity in the final composition for the intended application. The solution may contain from 0% to 98% by weight water-soluble, polar organic compound. The polar organic compound may be a polyhydric alcohol monomer or polymer. Low molecular weight polyoxyethylene glycols are suitable (average M.W. 200 to 600 e.g., Carbowax TM 200 and 600 available from Union Carbide). Glycerol is preferred. The plasticizing electrically-conductive solution may also contain from 2% to 100% water. Additionally the solution may contain up to 12% by weight of soluble salt such as a halide. The chloride, iodide, and bromide salts of sodium and potassium may conveniently be used. Particularly preferred is potassium chloride.

The ratio of soluble polar organic compound to water and the concentration of salt may be varied depending on the rheological and electrical properties desired. Suitable ratios of organic compound to water are 4:1, 2:1, and 1:1. Preferably water comprises at least 20%, and most preferably 25%, by weight, of the total composition. Preferably the salt may comprise from 0% to 6% by weight of the plasticizing, electrically-conductive solution. Those skilled in the art of biomedical electrodes appreciate that when the polymer matrix is about 30% neutralized a small amount of water and no soluble salt in the plasticizing solution will result in a final adhesive that is sufficiently electrically-conductive for use on grounding plate electrodes. In contrast, the preferred salt, potassium chloride, in a concentration of 1.25% by weight of the plasticizing, electrically-conductive solution is preferred where the intended use is on monitoring electrodes having the ability to recover from potential overloads applied during defibrillation.

The preferred composition has light covalent crosslinking. In that case the adhesive precursor includes a multifunctional monomer. Suitable crosslinkers include triethylene-glycol-bis-methacrylate (TEGBM), ethylene-glycol-bis-methacrylate, methylene bis-acrylamide, triethylene-glycol-bis-acrylate, and 3,3'-ethylidene-bis (N-vinyl-2-pyrrolidone). Additional crosslinkers are listed in U.S. Pat. No. 4,536,554. The amount of crosslinker may be varied depending on the choice of monomers and crosslinkers and the polymerization conditions. When the monomers are acrylic acid and N-vinyl-pyrrolidone, the crosslinker is preferably TEGBM, 3,3-ethylidene-bis-(N-vinyl-2-pyrrolidone) or methylene bisacrylamide. Crosslinker levels from 0.25% to 0.625% by weight of total monomers may be conveniently used. The most preferred crosslinker is TEGBM present at a level of 0.625% by weight of total monomers.

The polymerization may be started with an initiator of either the photo or thermal class. Photo initiators are preferred. Examples of useful photo initiators are disclosed in the article "Photo Initiators—An Overview" by Berner et al., in the Journal of Radiation Curing (April 1979), pp. 2 through 9. The preferred photo initiator is benzildimethylketal. Examples of useful thermal initiators are benzoyl peroxide, azo-bis-isobutyronitrile, di-t-butyl peroxide and bromyl peroxide. The actual selection of initiator is dependent on the monomers and other components of the adhesive precursor.

The preferred electrically-conductive adhesive displays excellent rheological and electrical properties. A biomedical electrode having a suitable conductor, e.g. silver silver/chloride, and incorporating the preferred composition meets the defibrillation recovery potential standards set forth in the AAMI voluntary standard "American National Standard for Pregelled ECG Disposable Electrodes" published by the Association for Advancement of Medical Instrumentation. Electrodes incorporating the preferred composition as the only adhesive may be used as diagnostic electrodes. Electrodes incorporating the preferred composition and a medical tape can be used for extended monitoring without excessive drying. In both cases the electrical properties are improved with observation of reduced skin impedance and adhesive properties are substantially improved with better tack and no residue upon removal.

The biomedical electrode of the present invention comprises a conductor and a layer of the electrically-conductive, pressure-sensitive adhesive composition in electrical contact with the conductor. The conductor is configured to be attachable to an electromedical instrument. Those skilled in the art are familiar with numerous stud and eyelet constructions, and with metallic foils and polymeric substrates coated with a thin layer of conductive metal or a conductive metal and metal salt, e.g., aluminum, tin, silver/silver chloride. The conductor may also be an electrically active form of carbon, e.g., graphite.

The electrically-conductive, pressure-sensitive adhesive has two surfaces; one contacts the conductor, and the second functions in use to contact and adhere to a patient's skin. When the biomedical electrode is to be used as a patient grounding plate or a long term (e.g, at least 3 days) monitoring electrode, a medical tape comprised of a backing coated with a biocompatible pressure-sensitive adhesive may be added to the surface of the conductor opposing the electrically-conductive, pressure-sensitive adhesive with an apron of medical tape extending beyond the periphery of the conductor. The medical tape assists in holding the electrode to the skin and in the case of grounding plate electrodes serves to insulate the conductor surface from direct electrical contact with the patient and to prevent current flow along short circuits (e.g. blood or water).

When the biomedical electrode is a diagnostic electrode the conductor is preferably a polymeric substrate (e.g., polyester) coated with, or laminated to tin. The conductive adhesive is made by the photoinitiated polymerization of an adhesive precursor. The preferred adhesive precursor comprises by weight about 10% hydrogen bond donating monomer (preferably acrylic acid); 10% hydrogen bond accepting monomer (preferably N-vinyl-pyrrolidone); 0.125% crosslinker (preferably TEGBM); 0.07% photoinitiator (preferably benzildimethylketal available as Irgacure TM 651, Ciba Giegy), 1% soluble salt (preferably potassium chloride); 25.5% water and 53.3% glycerol. The acrylic acid is 50% neutralized preferably with sodium hydroxide. The layer of pressure-sensitive adhesive is preferably coated on the tin over a surface area of about 1 in² (6.5 cm²) to a thickness of about 35 mils.

When the biomedical electrode is a monitoring electrode, the conductor is preferably a polymeric substrate coated with metallic silver and a thin layer of silver chloride. The electrically-conductive adhesive is preferably the same as recited above for a diagnostic electrode. The electrode preferably meets the AAMI voluntary standards for polarization recovery referenced above and described below in the examples.

When the biomedical electrode is a patient grounding plate the conductor is preferably an aluminum foil or a polymeric film coated with or laminated to aluminum. The electrically-conductive adhesive is formed by the photoinitiated polymerization of an adhesive precursor. The adhesive precursor comprises by weight about 10% hydrogen bond donating monomer (preferably acrylic acid); about 10% hydrogen bond accepting monomer (preferably N-vinyl-pyrrolidone), 0.125% crosslinker (preferably TEGBM), 0.07% photoinitiator (preferably benzildimethylketal available as Irgacure TM 651, Ciba Giegy), 25.5% water and 54.3% glycerol. The hydrogen bond donating monomer is preferably 20%–50% neutralized with sodium hydroxide.

DETAILED DESCRIPTION OF THE PREFERRED EMBODIMENTS

The composition of the present invention is preferably made with a photoinitiated polymerization of monomers dissolved in the plasticizing, electrically-conductive solution. In this process essentially all the materials present in the precursor are present in the same or modified form in the final composition. The plasticizing, electrically-conductive solution serves as a solvent for the monomers in the polymerization step and is present as the plasticizing, electrically-conductive liquid in the final composition. The monomers are converted in the polymerization to a copolymer matrix which may be, but need not be, covalently crosslinked. Preferably, a bifunctional crosslinking monomer is included and polymerization is carried to greater than 99% completion leaving less than 1% monomer in the final composition. The process may be carried out in situ with the adhesive precursor coated on an electrode conductor or backing substrate. Alternatively, the adhesive precursor can be coated on a transfer sheet to make a web of adhesive which subsequently may be incorporated into a composite such as a biomedical electrode. In either case, the adhesive precursor is preferably coated and cured on a thin scrim, e.g., 4 mils Cerex TM (Monsanto), to facilitate mechanical handling in manufacturing processes.

Figure 1:
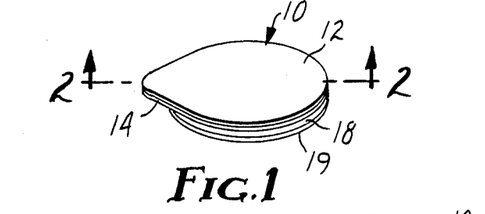
FIG. 1 is a perspective view of a diagnostic biomedical electrode of the present invention.
Figure 2:
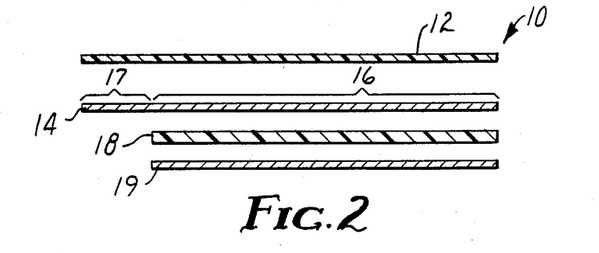
FIG. 2 is an exploded sectional view of the diagnostic biomedical electrode of the present invention through line 2—2 of FIG. 1.

The composition is preferably incorporated into a biomedical electrode. FIGS. 1 and 2 show a diagnostic biomedical electrode 10 according to the present invention. The preferred electrode 10 comprises a polymeric substrate 12, e.g. polyester, coated on one side with tin 14. A layer 18 of electrically-conductive adhesive composition coats a first portion 16 of the tin surface while a second portion 17 of the tin surface is a strip along one edge of the surface and free for attachment to a leadwire of an electromedical sensing device. Optional release liner 19 protects the electrically-conductive, pressure-sensitive adhesive 18 prior to use. The preferred electrode when tested in pairs face-to-face as described below, exhibits an impedance in ohms at 10 Hz not exceeding 2,000 ohms. The impedance preferably should not exceed 1,000 ohms. These performance levels are met with a diagnostic electrode having a conductive adhesive surface area of 1 in² (6.5 cm²) and a conductive adhesive thickness of 35 mils.

The preferred electrically-conductive adhesive for a diagnostic electrode is made from an adhesive precursor having by weight 10% acrylic acid (50% neutralized with sodium hydroxide), 10% N-vinyl-pyrrolidine, 0.125% TEGBM, 0.07% benzildimethylketal (Irgacure TM 651, Ciba Giegy), 1% potassium chloride 25.5% water and 53.5% glycerol.

The relative proportions and total amount of monomer, the total amount of crosslinker, the degree of neutralization of the hydrogen bond donating monomer, the amount of soluble salt and the ratio of water to polar organic liquid may all be varied with acceptable results. As the amount of crosslinker is reduced or eliminated the amount of hydrogen bond donating and accepting sites should be increased. Accordingly, when no crosslinker is used the total amount of solids is increased, for example to 30%, and the degree of neutralization of the hydrogen bond donating monomer is decreased for example to about 5% of the available sites.

Figure 3:
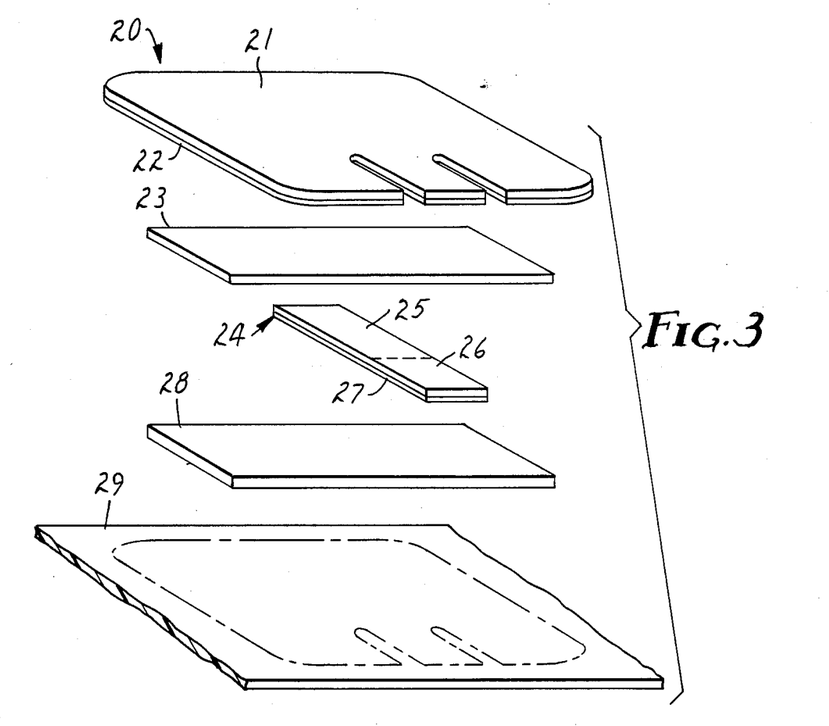
FIG. 3 is an exploded perspective view of a monitoring biomedical electrode of the present invention.

A preferred monitoring biomedical electrode 20 of the present invention is shown in FIG. 3. That electrode construction is described and claimed in commonly assigned application Ser. No. 865,521 filed May 21, 1986 (now U.S. Pat. No. 4,694,835). The monitoring electrode 20 has a backing 21 coated with biocompatible pressure-sensitive adhesive (PSA) 22. The backing 21 and biocompatible PSA 22 are formed with two cutouts along one edge so that the edge has three tabs. A bonding sheets 23 adheres to a portion of the biocompatible PSA 22. The bonding sheet 23 is aligned transverse to the cutout along one edge of the backing 21 and biocompatible PSA 22.

An electrical conductor 24 is comprised of a conformable film (e.g. polyester) that has been coated with a primer comprises of a binder and powder particles and therafter coated with metallic silver. The metallic silver is then treated to convert a portion of the surface layer to silver chloride. The preferred electrical conductor is described and claimed in commonly assigned application Ser. No. 865,521 filed May 21, 1986 still pending. The electrical conductor 24 is aligned transverse to the length of the bonding sheet 23 and preferably along the center of the three edge tabs on the backing and biocompatible PSA.

The conductor is shown in FIG. 3 with the conformable polymeric film face adjacent the bonding sheet 23 and a portion of the biocompatible PSA 22. For purposes of clarity the film face of conductor 24 is divided into two portions. Portion 25 spans the bonding sheet while portion 26 adheres to a portion of the biocompatible PSA 22. The silver/silver chloride surface 27 opposing portion 26 is free for attachment to a leadwire.

A web of electrically-conductive pressure-sensitive adhesive 28 is aligned with the bonding sheet. It adheres to and has electrical contact with that portion of the conductor 24 underlying the bonding sheet 23. The remainder of the web of conductive adhesive adheres to the bonding sheet 23. An optical release liner 29 protects the exposed surfaces of biocompatible PSA 22 and the web of electrically-conductive adhesive 28.

The preferred monitoring electrode will adhere to skin for at least three days without excessive drying of the adhesive (and concomitant loss of electrical performance). It can be removed without leaving an adhesive residue, and it meets the voluntary AAMI Standards for overload polarization recovery. The preferred monitoring electrode meets these performance requirements when the silver metal surface has a layer of silver chloride equivalent to at least about 30 mC, the electrically-conductive adhesive contains about 0.5% chloride ion, and the adhesive is made with the same precursor described above for the preferred diagnostic electrode.

Figure 4:
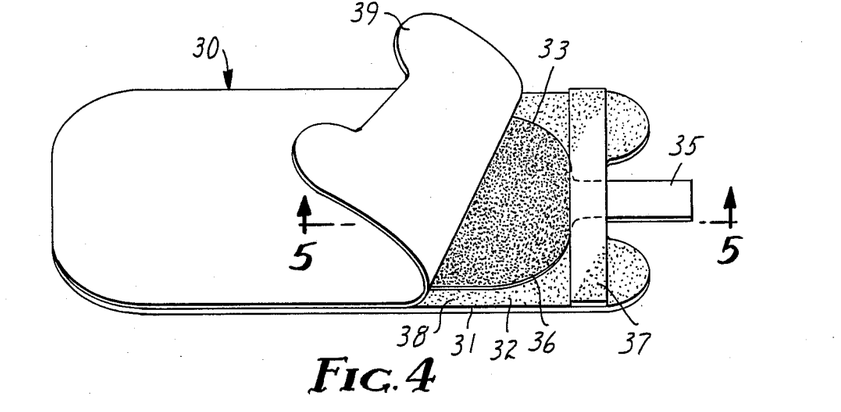
FIG. 4 is a perspective view of a grounding plate biomedical electrode of the present invention.
Figure 5:
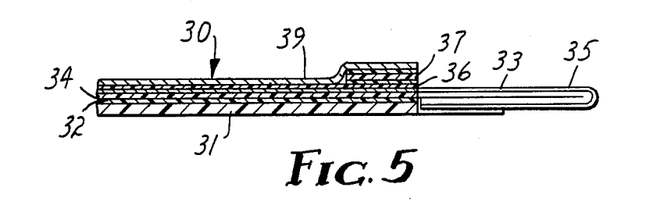
FIG. 5 is a sectional view of the grounding plate biomedical electrode of the present invention through line 5—5 of FIG. 4.

A preferred patient grounding plate biomedical electrode is shown in FIGS. 4 and 5. The preferred grounding plate biomedical electrode 30 comprises an insulating backing 31 coated on one surface with a biocompatible PSA 32. The backing 31 may be a closed cell vinyl foam. An electrode plate 33 adheres to a portion of the biocompatible PSA 32. The electrode plate may be an aluminum foil or a conformable polymeric backing 34, e.g., polyester, having aluminum deposited on one surface. The electrode plate 33 has an integrally associated connector tab 35 suited to electrically connect the grounding plate biomedical electrode to a leadwire which in use is connected to an electrosurgery generator. A web of electrically-conductive adhesive 36 coats the entire electrically-conductive surface of electrode plate 33 except the connector tab 35. An insulating strip 37 covers that portion of the surface of the connecting tab 35 which underlies the backing 31 and biocompatible PSA 32. The backing 31 and biocompatible PSA 32 have an apron 38 extending beyond the periphery of the electrode plate 33 and electrically-conductive adhesive 36. Those skilled in the art will appreciate that the apron 38 together with insulating strip 37 serves to insulate the electrode plate from direct contact with a patient's skin thereby avoiding thermal burns and from contact with other conductors (e.g. blood or water) which may result in an electrical short circuit. An optional release liner 39 may be used to protect adhesive surface prior to use.

The preferred grounding plate biomedical electrode has excellent adhesion and low impedance electrical contact with a patient's skin (to avoid hot spots or loss of contact due to motion). These performance criteria are met when the surface area of the electrically-conductive adhesive 36 and electrode plate 33 are 20 in$^2$ (130 cm$^2$), the electrically-conductive adhesive 36 is coated 20 mils thick, and the electrically-conductive adhesive is made from a precursor having by weight 10% acrylic acid (20–50% neutralized with sodium hydroxide), 10% N-vinylpyrrolidone, 0.125% TEGBM, 0.07 benzildimethyketal Irgacure No. 651, Ciba Giegy), 25.5% water and 54.4% glycerol.

A further understanding of the benefits and versatility of the electrically-conductive adhesive of the present invention and biomedical electrodes incorporating that adhesive will be appreciated from the following non-limiting examples.

In the examples, the following procedures are used.

PROCEDURE A

Adhesive Preparation

The soluble salt (if any) is added to water in a glass container and dissolved. Neutralizing base is added and dissolved. Thereafter the water-soluble polar organic compound is added and dissolved.

In a separate container the hydrogen bond donating monomer is mixed with the polymerization initiator and crosslinker (if any).

The salt, water, polar organic compound solution is mixed with the hydrogen bond donating monomer mixture. Just prior to coating on a substrate, the hydrogen bond accepting monomer is dissolved in the mixture and polymerization is initiated.

The adhesive precursor is coated on a substrate and exposed to U.V. radiation in a nitrogen atmosphere for time sufficient to complete polymerization. Immediately following polymerization the composition is visually inspected for opacity which is noted as phase separation.

PROCEDURE B

Initial Tack

Immediately following polymerization the composition is evaluated for initial tack. In this test firm pressure is applied to the sample with a thumb and the thumb is removed. The samples are rated as follows:

0: very soft, poor tack, residue on thumb upon removal
1: soft, poor tack, small amount of residue on thumb
2: moderately soft, acceptable tack, no residue
3: moderately soft, good tack, no residue
4: moderately firm, acceptable tack, no residue
5: very firm, little or no tack

PROCEDURE C

Impedance

Impedance in ohms of an electrode is measured using a Model 4800A Vector Impedance Meter manufactured by Hewlett Packard, Palo Alto, Calif. Measurements are conducted in the conventional manner on electrode pairs connected face-to-face (adhesive-to-adhesive) using a low level signal suitable for measurements on ECG electrodes. The impedance of the electrode at 10 Hz is recorded.

PROCEDURE D

Polarization Potential

Figure 6:
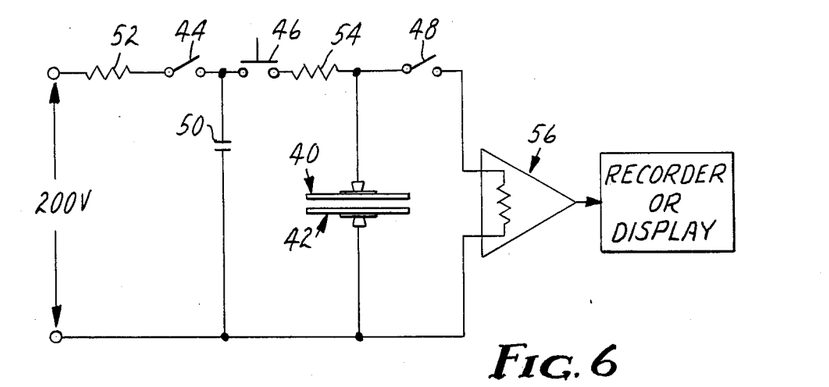
FIG. 6 is a circuit diagram for use in a defibrillation overload recovery test.

The polarization potential of an electrode is determined using the procedure and circuit described in the AAMI Test Standard "American National Standard for Pregelled ECG Disposable Electrodes" published by the Association for Advancement of Medical Instrumentation. The circuit is shown in FIG. 6.

1. Two electrodes 40 and 42 are connected adhesive-to-adhesive and connected to the test circuit (FIG. 6) with switch 44 closed and switches 46 and 48 open.

2. At least 10 seconds are allowed for the capacitor 50 to fully charge to 200 V; switch 44 is then opened.

3. The capacitor 50 is discharged through the electrode pair by holding switch 46 closed long enough to discharge the capacitor 50 to less than 2 V. This time is no longer than 2 seconds.

4. Switch 48 is closed immediately, and the electrode pair is connected to the offset potential measurement system (switch 46 open).

5. The electrode offset potential is recorded to the nearest 1 mV, 5 seconds after the closure of switch 48 and every 10 seconds thereafter for the next 30 seconds. The overload and measurement is repeated three times.

In the test circuit (FIG. 6), resistor 52 has a resistance of 10 kilohms, and resistor 54 is a 5 watt, 100 ohm resistor. Capacitor 50 has a capacitance of 10 $\mu$F. All capacitors and resistors are within 90 to 110 percent of the specified values. The offset recorder input amplifier 56 has a resistance of 10 megaohms and has an input impedance from 0 to 10 Hz of 10 M$\Omega$, $\pm$10 percent, and a bias current of less than 200 nA. The error of the voltage-recording equipment is no greater than $\pm$5 percent of full scale of 100 mV. A 10 mV change is measurable with an error no greater than $\pm$1 mV. For this purpose, the full scale range and resolution of the recording instrument may be adjusted as needed. The test sequence (steps 1-5) is repeated for 3 electrode pairs. The polarization potential noted for an electrode of a particular construction is the numerical average of the potentials measured 15 seconds after the fourth pulse for each of the three sample pairs.

EXAMPLE 1

The preferred homogeneous pressure-sensitive electrically-conductive adhesive of the present invention was made following Procedure A. The reaction mixture was coated to a thickness of 35 mils on a silicone coated release paper (HP Smith). A scrim (Cerex TM, Monsanto) was impregnated into the reaction mixture prior to polymerization. Polymerization was accomplished by exposing the precursor to UV irridation (360 nM lamp available from General Electric) for four minutes under a nitrogen atmosphere. No opacity was observed. Following Procedure B, the initial tack of the adhesive composition was rated 3. The constituents of the precursor and their relative amounts are shown in Table I.

TABLE I

| Constituents | Amount By Weight |
| --- | --- |
| Acrylic Acid | 10% |
| N—vinylpyrrolidone | 10% |
| Glycerol | 50.6% |
| Water | 25.5% |
| benzildimethylketal | 0.07% |
| TEGBM | 0.125% |
| KCl | 1.0% |
| NaOH | 2.77% |

EXAMPLE 2

The adhesive composition made in Example 1 was used to make a diagnostic electrode. The electrical conductor was a polyester film having a continuous layer of tin laminated to one surface. The conductor had a surface area slightly larger than 1 in$^2$ (6.5 cm$^2$). A web of adhesive having a surface area of 1 in$^2$ (6.5 cm$^2$) together with the silicone coated transfer sheet on which it was formed was laminated to the tin surface of the conductor. A steel roller was passed back and forth over the composite once to assure good wetting of the tin by the adhesive.

The electrodes were tested for impedance using Procedure C. The face to face impedance is 900$\Omega$.

EXAMPLE 3

The adhesive composition made in Example 1 is used in the construction of a monitoring electrode as described above and shown in FIG. 3. The backing is a polyethylene foam having closed cells (Voltek, Inc., Lawrence NH) and has a surface area of 3.5 in$^2$. The biocompatible pressure-sensitive adhesive is based on a copolymer of isoctyacrylate (90%) and N-vinylpyrrolidone (9% by weight) and is coated 11.5 grains/in$^2$ (48 g/m$^2$). The bonding sheet is a spun bonded nylon (Monsanto, St. Louis, MO), the electrical conductor is made with conformable polyester backing coated with a primer comprised of binder and particles (commercially available as Imperial TM Lapping Film, 3M St. Paul, MN). Silver is vapor deposited on the film and a portion of the silver is converted to silver chloride. The conductor measures 1.25" by 0.5". The electrically-conductive adhesive web measures 2" by 0.75" and is 35 mils thick.

Impedance and polarization potentials were tested using procedures B and C on these monitoring electrodes. Table II summarizes the results.

TABLE II

| | |
|---|---|
| Offset, mV | 0.6 |
| 10 Hz impedance, ohms | 150 |
| 100K Hz impedance, ohms | 50 |
| Polarization potential, mV | |
| 5 sec, 1st discharge | 20.8 |
| 5 sec, 2nd discharge | 16.6 |
| 5 sec, 3rd discharge | 14.9 |
| 5 sec, 4th discharge | 13.8 |
| Trace quality | very good |

EXAMPLE 4

A wide range of samples are made following procedure A. The total weight of the two monomers studied varies from 12% to 50%. The ratio of the two monomers is varied within each total weight of monomer studied. Each 100 g precursor contains 1.0 g KCl, 25.5 g $H_2O$, NaOH (in an amount sufficient to neutralize 50% of the acid groups), 0.07 g benzildimethylketal, 0.125 g TEGBM, acrylic acid (AA), N-vinylpyrrolidone (NVP), and glycerol (balance). Procedure B is used to describe initial tack. The results are summarized in Table III. An asterisk (*) indicates observation of patches of opacity.

TABLE III

| Percent Monomer | 100% AA | 1/.11 | 1/.25 | 1/.42 | 1/.66 | 1/1 | 1/1.5 | 1/2.3 | 1/4 | 1/9 | 100% NVP |
|---|---|---|---|---|---|---|---|---|---|---|---|
| 12 | 0 | | | | | | | | | | |
| 18 | 2 | 1.5 | | | | | | | | | |
| 20 | 5* | 4* | 4* | 3 | 3 | 3 | 2 | 1 | 1* | 0 | 0 |
| 30 | 5* | | 4 | | 3.5 | | 3 | | 2 | | 1 |
| 40 | | | | | | | | | 3.5 | | 1 |
| 50 | | | | | | | | | 5* | | 1 |

EXAMPLE 5

Eight samples, ranging from 0% to 100% neutralization are made according to Procedure A. In each 100 g sample the reaction mixture contains 10 g acrylic acid, 10 g N-vinylpyrrolidone, 1.0 KCl, 0.07 benzildimethylketal, 0.125 g TEGBM, 25.5 g $H_2O$, NaOH (in an amount sufficient to result in the degree of neutralization), and glycerol (balance). Using procedure B to describe tack, the results are summarized in Table IV. An asterisk (*) indicates phase separation observed as patches of opacity.

TABLE IV

| Sample # | Percent Neutralization | Tack |
|---|---|---|
| 1 | 0 | 5* |
| 2 | 5 | 3.5 |
| 3 | 20 | 3 |
| 4 | 40 | 3 |
| 5 | 60 | 2 |
| 6 | 80 | 2 |
| 7 | 95 | 1.5 |
| 8 | 100 | 0* |

EXAMPLE 6

Nine samples are made following procedure A. Each 100 g reaction mixture contains 10 g acrylic acid, 10 g N-vinylpyrrolidone, 2.77 g NaOH, 1.0 g KCl, 0.07 g benzildimethylketal, 0.125 g TEGBM, water and glycerol. The ratio of water to glycerol is varied over a wide range while keeping all other components at at constant level. The samples are evaluated for initial tack using Procedure B and the results are summarized in Table V. An asterisk (*) indicates patches of opacity.

TABLE V

| Sample # | Glycerol (g) | Water (g) | Tack |
|---|---|---|---|
| 1 | 76.1 | 0 | 3 |
| 2 | 66.1 | 10 | 2 |
| 3 | 56.1 | 20 | 3 |
| 4 | 46.1 | 30 | 3 |
| 5 | 36.1 | 40 | 4 |
| 6 | 26.1 | 50 | 4 |
| 7 | 16.1 | 60 | 4* |
| 8 | 6.1 | 70 | 4* |
| 9 | 0 | 76.1 | 4 |

EXAMPLE 7

Five samples, with different amounts of salt incorporated, are made according to Procedure A. Each 100 g reaction mixture contains 10 g acrylic acid, 10 g N-vinylpyrrolidone, 2.77 g NaOH, KCl, 0.07 g benzildimethylketal, 0.125 g TEGBM, 25.5 g $H_2O$ and glycerol (balance). Using procedure B to describe tack, results are summarized in Table VI. An asterisk (*) indicates opacity.

TABLE VI

| Sample # | g KCl | Tack |
|---|---|---|
| 1 | 3 | 3 |
| 2 | 6 | 2 |
| 3 | 9 | 5* |
| 4 | 0 | 3 |
| 5 | 1 | 3 |

EXAMPLE 8

Samples are made following Procedure A using different crosslinkers and levels of crosslinkers ranging from 0.0125% to 0.5%. The crosslinkers include triethylene-glycol-bismethacrylate (TEGBM), 3,3-ethylidene-bis-(n-vinyl pyrrolidone) (EBVP), and methylenebisacrylamide (MBA). Each 100 g reaction mixture contains 10 g acrylic acid, 10 g N-vinylpyrrolidone, 1 g KCl, 0.07 benzildimethylketal, crosslinker, 25.5 g water, and glycerol (balance). Using procedure B to evaluate initial tack, the results are summarized in Table VII.

TABLE VII

| Sample # | Crosslinker (g) | | Tack |
|---|---|---|---|
| 1 | TEGBM | 0.05 | 1 |
| 2 | TEGBM | 0.1 | 3 |
| 3 | TEGBM | 0.3 | 4 |
| 4 | TEGBM | 0.5 | 5 |
| 5 | EBVP | 0.0125 | 1 |
| 6 | EBVP | 0.025 | 3 |
| 7 | EBVP | 0.075 | 4 |
| 8 | EBVP | 0.125 | 3 |
| 9 | MBA | 0.0125 | 1 |
| 10 | MBA | 0.025 | 3 |
| 11 | MBA | 0.075 | 4 |

TABLE VII-continued

| Sample # | Crosslinker | (g) | Tack |
| --- | --- | --- | --- |
| 12 | MBA | 0.125 | 5 |

EXAMPLE 9

A variety of samples are made following Procedure A in which different hydrogen bond donating and hydrogen bond accepting monomers are used. Each 100 g reaction mixture contains monomers, 1 g KCl, 0.07 g benzildimethylketal, 0.125 g TEGBM, 25.5 g water and glycerol (balance). The hydrogen bond donating monomers used are acrylic acid (AA), itaconic acid (ITA), and maleic acid (MA) with sufficient sodium hydroxide to neutralize 50% of the acid groups. The hydrogen bond accepting monomers used are N-vinylpyrrolidone (NVP) and dimethyl acrylamide (diMeA). Using Procedure B to describe tack, the results are summarized in TABLE VIII.

TABLE VIII

| Monomers | Tack |
| --- | --- |
| AA (10 g)/diMeA (10 g) | 3 |
| AA (14 g)/diMeA (6 g) | 3 |
| AA (6 g)/diMeA (14 g) | 3 |
| AA (15 g)/diMeA (15 g) | 4 |
| AA (20 g)/diMeA (20 g) | 4 |
| AA (8 g), ITA (2 g)/NVP (10 g) | 2 |
| AA (9 g), MA (1 g)/NVP, (10 g) | 2 |

EXAMPLE 10

Four samples are made following Procedure A. Each 100 g reaction mixture contains 10 g acrylic acid, 10 g N-vinylpyrrolidone, 2.77 g NaOH, 1 g KCl, 0.07 g benzildimethylketal, 0.125 g TEGBM, and 50.6 g polar organic compound. Using procedure B to describe tack, the results are summarized in Table IX.

TABLE IX

| Sample # | Glycerol (g) | Sorbitol (g) | Carbowax 200 (g) | Tack |
| --- | --- | --- | --- | --- |
| 1 | 25.3 | 25.3 | — | 4 |
| 2 | 37.9 | 12.6 | — | 3 |
| 3 | 25.3 | — | 25.3 | 3 |
| 4 | 37.9 | — | 12.6 | 2 |

EXAMPLE 11

The following describes the method for the thermal polymerization of the adhesive precursor material.

The procedure for making the sample is identical to that described in Procedure A except that potassium persulfate (the thermal initiator) is dissolved in the water. Table X shows the relative amounts of each component. The adhesive precursor is coated on a substrate and exposed to 50° C. for approximately 8 hours in a nitrogen atmosphere. Following Procedure B the initial tack of this thermally polymerized adhesive is rated 1.

TABLE X

| Constituent | Amount by Weight (Percent) |
| --- | --- |
| Acrylic acid | 10 |
| n-vinylpyrrolidone | 10 |
| Glycerol | 50.2 |
| Water | 25.5 |
| Potassium persulfate | 0.4 |
| TEGBM | 0.125 |
| KCl | 1.0 |
| NaOH | 2.77 |

EXAMPLE 12

Adhesion of the preferred diagnostic electrode to skin is compared to that of commercially available electrodes. One electrode tested is the Littmann 2322 diagnostic electrode (3M, St. Paul, MN). That electrode has a tin laminated to polyester conductor and a conductive adhesive like those described in U.S. Pat. No. 4,544,824. Another electrode compared is the Sentry Silver Sircuit #10009 (Sentry Medical Products, Santa Ana, CA). The package indicates that the Sentry Silver sircuit electrode has a silver/silver chloride conductor and a polyhesive conductive adhesive. The polyhesive conductive adhesive (Valleylab Inc., Boulder, CO) is believed to be made according to the disclosure of U.K. Appln. No. 2,115,431.

Samples of the electrodes to be tested are placed on the subject's back in horizontal rows. The electrodes are then pressed onto the skin using a rubber roller to ensure even contact. Immediately after application of the array of electrodes, they are removed one at a time beginning with the first electrode applied. To remove an electrode, a clip and a cord are used to attach one edge of the electrode to an instrument capable of pulling on the cord and measuring the force requried versus time. The electrode is pulled at an angle of 180° back across itself at a speed of 6 in./min. The force to peel the electrode from the skin is recorded. The maximum value corrected for the width of the electrode is reported as the skin adhesion. Because skin varies greatly from individual to individual and from place to place on a single individual, the test is conducted many times. The values reported in Table XI are numerical averages of the number of replicates shown in parentheses. The absolute values are not considered particularly significant. The rank of values within a panel is considered significant. In the panels performed, the rank from low to high is consistently Silver Sircuit TM electrodes followed by Littmann 2322 electrodes followed by electrodes with the adhesive of the present invention.

TABLE XI

| Panel | Average Skin Adhesion g/in (Replicates) | | |
| --- | --- | --- | --- |
| | Silver Sircuit | Littmann | New Adhesive |
| 1 | 19.5 (36) | 37.8 (36) | 74.1 (36) |
| 2 | 48.3 (24) | 69.6 (28) | — |
| 3 | 36.6 (32) | 72.4 (32) | — |
| 4 | — | 44.7 (18) | 103 (24) |
| 5 | — | 63.8 (35) | 96.3 (36) |

The foregoing description has been directed to preferred embodiments for the purposes of illustration and explanation. Those skilled in the art will appreciate that many modifications and changes will be possible without departing from the scope and spirit of the invention. The following claims are intended to embrace all such modifications and variations.

I claim:

1. A composition comprising:
   a conformable, cohesive, adhesive copolymer matrix formed by free radical polymerizing an adhesive precursor comprising a carboxylic acid as a water-soluble hydrogen bond donating monomer, N-vinyl pyrrolidone as a water-soluble hydrogen bond accepting monomer, and a polymerization initiator, wherein the molar ratio of hydrogen bond accepting sites to hydrogen bond donating sites available on the monomers is from about 1:3 to about 6:1 and wherein the weight ratio of carboxylic acid to N-vinyl pyrrolidone is from about 1:2 to about 3:1; and a plasticizing, electrically-conductive solution comprised of from about 0 to 98% by weight water-soluble, polar organic compound, about 2 to 100% by weight water, and about 0 to 12% by weight water-soluble salt;

wherein the composition contains from about 12% to about 50% by weight non-volatile copolymer matrix, the hydrogen bond donating sites on the copolymer matrix are from about 5% to about 80% neutralized, and the composition is substantially homogeneous and pressure-sensitive adhesive.

2. The composition of claim 1 wherein the copolymer matrix is covalently crosslinked and the adhesive precursor further comprises a multifunctional crosslinker present up to about 2.5% by weight of the total monomers in the adhesive precursor.

3. The composition of claim 1 wherein the hydrogen bond donating monomer is selected from the group of carboxylic acids consisting of α,β-ethylenically unsaturated carboxylic acids having up to eight carbon atoms.

4. The composition of claim 1 wherein the hydrogen bond donating monomer is acrylic acid and the final composition comprises from about 15% to about 25% by weight copolymer matrix.

5. The composition of claim 1 wherein the water-soluble, polar organic compound is selected from a group consisting of monomeric and polymeric polyhydric alcohols.

6. The composition of claim 1 wherein the water-soluble polar organic compound is glycerol.

7. The composition of claim 1 wherein the soluble salt is a chloride, bromide, or iodide salt of sodium or potassium and comprises from 0 to 6% by weight of the plasticizing, electrically-conductive solution.

8. The composition of claim 1 wherein the soluble salt is potassium chloride and it comprises about 1.25% by weight of the plasticizing, electrically-conductive solution.

9. An electrically-conductive, pressure-sensitive adhesive formed by the free radical copolymerization of an adhesive precursor comprising:
a carboxylic acid as a water-soluble hydrogen bond donating monomer;
N-vinyl pyrrolidone as a water-soluble hydrogen bond accepting monomer;
a free radical initiator; and
a plasticizing, electrically-conductive solution comprised of from about 0 to 98% by weight water-soluble, polar organic compound, from about 2 to 100% by weight water, and from about 0 to 12% by weight soluble salt;
wherein the ratio of hydrogen bond accepting sites to hydrogen bond donating sites on the monomers is from about 1:3 to about 6:1, the weight ratio of carboxylic acid to N-vinyl pyrrolidone is from about 1:2 to about 3:1, the adhesive precursor contains from about 12% to about 50% by weight total monomers, the acid sites on the hydrogen bond donating monomer are from about 5% to about 80% neutralized, and the composition is substantially homogeneous and pressure-sensitive adhesive.

10. The composition of claim 9 wherein the adhesive precursor further comprises a multifunctional crosslinker present up to about 2.5% by weight of the total monomers in the adhesive precursor.

11. The composition of claim 9 wherein the hydrogen bond donating monomer is selected from the group of carboxylic acids consisting of α,β-ethylenically unsaturated carboxylic acids having up to eight carbon atoms.

12. The composition of claim 9 wherein the adhesive precursor comprises by weight:
from about 5% to 43.5% acrylic acid,
from about 7% to 45% N-vinylpyrrolidone,
from about 0.05% to 0.3% triethylene-glycol-bis-methacrylate,
from about 0.02% to 0.1% benzildimethylketal,
from about 5% to 60% water,
from about 0.5% to 12% potassium chloride, and
from about 30% to 70% glycerol; and wherein the acrylic acid is from about 5% to about 80% neutralized with sodium hydroxide.

13. The composition of claim 3 wherein the adhesive precursor comprises by weight
from about 8% to 12% acrylic acid
from about 8% to 12% N-vinylpyrrolidone
from about 0.10% to 0.15% triethylene-glycol-bis-methacrylate
from about 0.05% to 0.07% benzildimethylketal
from about 23% to 27% water
from about 0.75% to 1.25% potassium chloride
from about 48% to 52% glycerol, and the acrylic acid is from about 45% to 55% neutralized with sodium hydroxide.

14. A process for making an electrically-conductive, pressure-sensitive adhesive comprising:
(a) providing an adhesive precursor comprising a carboxylic acid as a hydrogen bond donating monomer, N-vinyl pyrrolidone as a hydrogen bond accepting monomer, a free radical initiator, and a plasticizing, electrically-conductive solution comprised of from about 0 to 98% by weight water-soluble organic compound, from about 2 to 100% by weight water, and from about 0 to 12% by weight soluble salt;
wherein the ratio of hydrogen bond accepting sites to hydrogen bond donating sites on the monomers is from about 1:3 to about 6:1, the weight ratio of carboxylic acid to N-vinyl pyrrolidone is from about 1:2 to about 3:1, the adhesive precursor contains from about 12% to about 50% by weight of total monomers, the hydrogen bond donating sites on the hydrogen bond donating monomer are from about 5% to about 80% neutralized, and the composition is substantially homogeneous and pressure-sensitive adhesive;
(b) coating the adhesive precursor on a substrate; and
(c) initiating copolymerization of the monomers in the adhesive precursor.

15. A biomedical electrode comprising:
an electrical conductor, means integrally associated with the conductor for connecting the electrode to an electromedical instrument, an electrically-conductive, pressure-sensitive adhesive in electrical contact with the conductor comprising a conformable, cohesive, adhesive copolymer matrix formed by free radical polymerizing an adhesive precursor comprising a carboxylic acid as a water-soluble hydrogen bond donating monomer, N-vinyl pyrrolidone as a water-soluble hydrogen bond accepting monomer, and a polymerization initiator, wherein the molar ratio of hydrogen bond accepting sites to hydrogen bond donating sites available on the monomers is from about 1:3 to about 6:1 and wherein the weight ratio of carboxylic acid to N-vinyl pyrrolidone is from about 1:2 to about 3:1, and a plasticizing, electrically-conductive solution comprised of from about 0 to 98% by weight water-soluble, polar organic compound, about 2 to 100% by weight water, and about 0 to 12% by weight water-soluble salt; wherein the electrically-conductive, pressure-sensitive adhesive contains from about 12% to about 50% by weight non-volatile copolymer matrix, the hydrogen bond donating sites on the copolymer are from about 5% to about 80% neutralized, and the composition is substantially homogeneous and pressure-sensitive adhesive.

16. The biomedical electrode of claim 15 further comprising a medical tape comprised of a backing and a biocompatible pressure-sensitive adhesive coated on one surface of the backing wherein the conductor adheres to a portion of the medical tape and the remainder of the medical tape extends beyond the perimeter of the conductor.

17. A method of making a biomedical electrode comprising:
(a) providing a web of conductor;
(b) covering the conductor with an electrically-conductive, pressure-sensitive adhesive comprised of a conformable, cohesive, adhesive copolymer formed by free radical polymerizing an adhesive precursor comprising a carboxylic acid as a water-soluble hydrogen bond donating monomer, N-vinyl pyrrolidone as a water-soluble hydrogen bond accepting monomer, and a polymerization initiator, wherein the molar ratio of hydrogen bond accepting sites to hydrogen bond donating sites available on the monomers is from about 1:3 to about 6:1 and wherein the weight ratio of carboxylic acid to N-vinyl pyrrolidone is from about 1:2 to about 3:1, and a plasticizing, electrically-conductive solution comprised of from about 0 to 98% by weight water-soluble, polar organic compound, about 2 to 100% by weight water, and about 0 to 12% by weight water-soluble salt; wherein the electrically-conductive, pressure-sensitive adhesive contains from about 12% to about 50% by weight non-volatile copolymer matrix, the hydrogen bond donating sites on the copolymer matrix are from about 5% to about 80% neutralized, and the composition is substantially homogeneous and pressure-sensitive adhesive; and
(c) cutting the laminate of steps a and b to form electrodes.

18. The method of claim 17 further comprising laminating onto the surface of the conductor opposing the electrically-conductive, pressure-sensitive adhesive a medical tape comprised of a backing and a biocompatible pressure-sensitive adhesive coated on one surface of the backing and cutting the medical tape to a shape and size that provides an apron of medical tape extending beyond the perimeter of the conductor.

* * * * *

UNITED STATES PATENT AND TRADEMARK OFFICE
CERTIFICATE OF CORRECTION

PATENT NO.  : 4,848,353
DATED       : July 18, 1989
INVENTOR(S) : Michael R. Engel It is certified that error appears in the above-identified patent and that said Letters Patent is hereby corrected as shown below:

| | | |
|---|---|---|
| Abstract, | Line 7,  | "a" should be --an--. |
| Abstract, | Line 11, | "compsition" should be --composition--. |
| Col. 2,   | Line 8,  | "0.1-1A" should be --0.5-1A--. |
| Col. 2,   | Line 19, | "on" should be --one--. |
| Col. 2,   | Line 36, | "polymerization" should be --polymerizable--. |
| Col. 2,   | Line 49, | "Engle" should be --Engel--. |
| Col. 3,   | Line 55, | "contaning" should be --containing--. |
| Col. 4,   | Line 35, | "0.5%" should be --5%--. |
| Col. 5,   | Line 48, | "electircally-conductive" should be --electrically-conductive--. |
| Col. 9,   | Line 19, | "sheets" should be --sheet--. |
| Col. 9,   | Line 25, | "comprises" should be --comprised--. |
| Col. 9,   | Line 26, | "therafter" should be --thereafter--. |
| Col. 9,   | Line 30, | delete "still pending" and insert therefor --, now U.S. Patent No. 4,694,835--. |

UNITED STATES PATENT AND TRADEMARK OFFICE
CERTIFICATE OF CORRECTION

PATENT NO. : 4,848,353

DATED : July 18, 1989

INVENTOR(S) : Michael R. Engel

It is certified that error appears in the above-identified patent and that said Letters Patent is hereby corrected as shown below:

Col. 10, Line 25, "surface" should be --surfaces--.

Col. 16, Line 19, "sircuit" should be --Sircuit--.

Col. 18, Line 25, "3" should be --9--.

Signed and Sealed this

Thirteenth Day of February, 1990

Attest:

JEFFREY M. SAMUELS

*Attesting Officer*  *Acting Commissioner of Patents and Trademarks*